United States Patent [19]

Dive et al.

[11] Patent Number: 5,677,281
[45] Date of Patent: Oct. 14, 1997

[54] USE OF PEPTIDE DERIVATIVES FOR THE PREPARATION OF MEDICAMENTS INHIBITING ENDOPEPTIDASES 24.15 AND 24.16

[75] Inventors: Vincent Dive, Vincennes; Flavio Toma, Clamart, both of France; Athanasios Yiotakis, Athens, Greece

[73] Assignee: Commissariat a l'Energie Atomique, Paris, France

[21] Appl. No.: 44,616

[22] Filed: Apr. 9, 1993

[30] Foreign Application Priority Data

Apr. 10, 1992 [FR] France .................................... 92 04429

[51] Int. Cl.$^6$ .................................................. A61K 38/05
[52] U.S. Cl. ................................. 514/18; 514/19; 514/7; 530/331; 548/535
[58] Field of Search ............................. 514/18, 19, 7; 530/331; 548/535

[56] References Cited

U.S. PATENT DOCUMENTS 4,558,034  12/1985  Galardy et al. ............................ 514/7

FOREIGN PATENT DOCUMENTS 0085 488  8/1983  European Pat. Off. .

OTHER PUBLICATIONS

A. Yiotakis, et al, Eu. J. Biochem., vol. 172, pp. 761–766 (1988).
Dive et al., Eur. J. Biochem. 191 (1990) pp. 685–693.

*Primary Examiner*—Cecilia J. Tsang
*Assistant Examiner*—David Lukton
*Attorney, Agent, or Firm*—Oblon, Spivak, McClelland, Maier & Neustadt, P.C.

[57] ABSTRACT

The invention relates to the use of peptide derivatives for the preparation of medicaments inhibiting endopeptidases 24.15 and 24.16.

These peptide derivatives are in accordance with the formula:

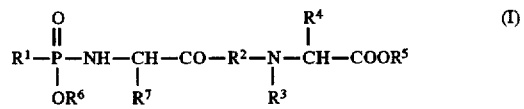

in which $R^1$ is an optionally substituted aralkyl group, $R^2$ is Pro, Hyp, thiazolidine or dehydroproline, $R^3$ is H or an alkyl radical, $R^4$ is an alkyl group or the side chain of an amino acid, $R^5$ and $R^6$ can be H, $NH_4+$ or metals and $R^7$ is H or $CH_3$.

N-(phenylethylphosphonyl)-Gly-Pro-aminohexanoic acid and N-(phenylethyl phosphonyl)-Ala-Pro-aminohexanoic acid are examples of effective derivatives.

13 Claims, 2 Drawing Sheets

USE OF PEPTIDE DERIVATIVES FOR THE PREPARATION OF MEDICAMENTS INHIBITING ENDOPEPTIDASES 24.15 AND 24.16

BACKGROUND OF THE INVENTION

1. Field of the Invention

The present invention relates to the use of peptide derivatives of the phosphonamide type for the preparation of medicaments inhibiting endopeptidases 24.15 and/or 24.16.

2. Description of the Related Art

Endopeptidases are enzymes belonging to the family of metallopeptidases containing zinc and which have the property of inactivating certain neuromodulators acting on the brain such as neurotensin and in this way destroying their pharmacological effects. In addition, these endopeptidase inhibitors would be of great interest for being able to potentiate the pharmacological effects associated with neurotensin.

It is known that certain dipeptides such as Pro-Ile are able to inhibit endopeptidase 24.16, as described by Dauch et al in Eur. J. Biochem., vol. 202, pp. 269-276, 1991b. However, this endopeptidase 24.16, inhibitor has a certain Ki inhibition of 90 µM, which is much too high, bearing in mind the solubility of this dipeptide, to permit its in vivo use. Moreover, it has no inhibiting action on endopeptidase 24.15 at a concentration as high as 5 mN.

However, for endopeptidase 24.15 a compound inhibiting said enzyme is known and which carries the formula:

CPP-Ala-Ala-Tyr-pAB with CPP representing the carboxy-3-phenylpropyl radical and pAB the p-aminobenzoate and having an inhibition constant of 16 nM, as described by Orlowski et al, Biochemistry, vol.27, pp. 597-602, 1988. Therefore this inhibitor is much more effective than the Pro-Ile inhibitor of endopeptidase 24.16, but does not apply to the latter. However, it has an inhibiting effect on endopeptidase 24.16 corresponding to a much too high inhibition constant of 1 µM, as described by Dauch et al in Biochem. J., 280, 1991, pp.421-426.

Research has also been undertaken for finding inhibitors which are more effective with respect to endopeptidases 24.16 and 24.15, which both hydrolyze neurotensin.

SUMMARY OF THE INVENTION

As a result of this research, it has been found that certain peptide derivatives described in FR-A-2 654 430, known to have an inhibiting effect, on bacterial collagenases such as the Clostridium Histolyticum collagenase had an even more marked and very specific inhibiting effect on endopeptidases 24.16 and 24.15. This effect is unexpected, because endopeptidases have a different specificity from that of bacterial collagenases and they have no recognized similarity with bacterial collagenases.

Thus, the present invention relates to the use of a peptide derivative of formula:

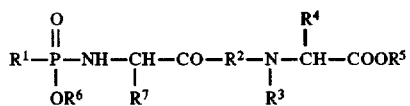

in which $R^1$ represents an aralkyl group, whose alkyl group has 1 to 3 carbon atoms, the aralkyl group being unsubstituted or substituted on its aryl part by at least one substituent chosen from among halo, trifluoromethyl, $C_1$ to $C_4$ alkoxy, $C_1$ to $C_4$ alkyl, $C_1$ to $C_4$ alkanoyloxy, $C_2$ to $C_5$ carbonyloxyalkyl, nitro, carboxy or cyano groups, $R^2$ is a divalent radical derived from an amino acid chosen from among proline, hydroxyproline, thiazolidine and dehydroproline of formula:

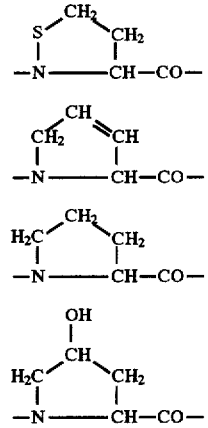

connected by its NH part to CO, $R^3$ is a hydrogen atom or a $C_1$ to $C_4$ alkyl group, $R^4$ is a $C_1$ to $C_5$ alkyl group or the side chain of an α-amino acid, $R^5$ represents a hydrogen atom, $NH_4+$, a pharmaceutically acceptable metal atom, a $C_1$ to $C_5$ alkyl group or a benzyl group, $R^6$ represents a hydrogen atom, $NH_4+$ or a pharmaceutically acceptable metal atom and $R^7$ represents H or $CH_3$, for the preparation of a medicament inhibiting endopeptidases 24.15 and/or 24.16.

BRIEF DESCRIPTION OF THE DRAWINGS

Other features and advantages of the invention can be gathered from the following examples, given in an illustrative and non-limitative manner with reference to the attached drawings, wherein show.

Figure 1:
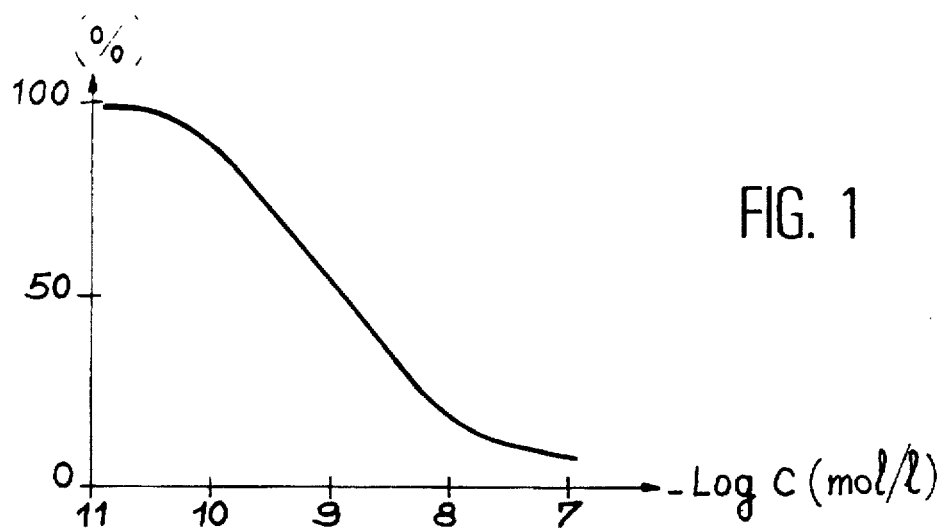
FIG. 1 A curve illustrating the percentage inhibiting effect of the peptide derivative on endopeptidase 24.16 as a function of the inhibitor concentration.

The medicament inhibiting endopeptidases 24.15 and/or 24.16 is a medicament potentiating the pharmacological effects associated with neurotensin. Therefore this medicament can be an analgesic, an anti-hypertensive agent or a hypothermal agent.

In the peptide derivatives described hereinbefore, the terms aryl, aralkyl and α-amino acid have the following meanings.

The term aryl designates systems having a carbocyclic and heterocyclic aromatic nucleus e.g. containing one or more heteroatoms such as O, S and N. These aryl groups generally have 3 to 10 carbon atoms. Examples of such aryl groups are phenyl, naphthyl, furyl, thienyl, pyrolyl, imidazolyl, pyridyl, pyrimidinyl, indolyl, quinolyl, oxazolyl and isooxazolyl groups.

The term aralkyl designates groups formed by the association of an aryl group and an alkyl group. The aryl groups can be of the type described hereinbefore. The alkyl groups can be straight or branched and have 1 to 3 carbon atoms. The aralkyl group can be substituted on its aryl part by at least one substituent chosen from among the halo groups, e.g. fluorine, chlorine, bromine or iodine, trifluoromethyl, $C_1$ to $C_4$ alkoxy, $C_1$ to $C_4$ alkyl, $C_1$ to $C_4$ alkanoyloxy, carbonyloxyalkyl with a $C_1$ to $C_4$ alkyl group, nitro, carboxy end cyano. In the same way, when $R^1$ represents an aryl group, it can also be substituted by the groups described hereinbefore.

The term α-amino acid used here relates to the twenty α-amino acids commonly found in proteins and which are also known under the name standard amino acids and their analogs. The side chains of these amino acids incorporate straight or branched alkyl groups, hydroxyalkyl, carboxyalkyl, aralkyl, aminoalkyl, carboxamide alkyl, mercapto alkyl, phenylalkyl, hydroxyphenylalkyl, guanidinoalkyl, imidazoylalkyl, indolylalkyl and pyrrolidinyl.

Examples of usable amino acids are alanine, arginine, asparagine, aspartic acid, cysteine, glutamine, glutamic acid, glycine, histidine, isoleucine, leucine, norleucine, lysine, methionine, phenylalanine, proline, hydroxyproline, serine, threonine, tryptophan, tyrosine, valine, nitrophenyl alanine, homoarginine, thiazolidine and dehydroproline.

In the peptide derivatives, the metals usable for $R^5$ and $R^6$ are pharmaceutically acceptable metals such as alkali metals and in particular sodium and lithium.

The peptide derivatives used in the invention can be prepared by conventional processes, particularly according to the process described in FR-A-2 654 430.

According to the invention, for the preparation of the medicament inhibiting endopeptidases 24.15 and/or 24.16, inclusion takes place of a pharmaceutically effective quantity of the peptide derivative of formula (I) given hereinbefore, in the pure state or in the form of the pharmaceutically acceptable salt, in a suitable, physiologically acceptable support or vehicle. This support can be a solution or suspension for injections.

It is also possible to use appropriate supports and excipients for obtaining a medicament intended for oral administration in the form of tablets or capsules, also incorporating, if necessary, conventional additives such as magnesium carbonate, magnesium stearate, talc, sugar, lactose, pectin, dextrin, starch, gelatin, tragacanth, methylcellulose, sodium carboxymethylcellulose, cocoa butter, etc. For this preparation it is also possible to add diluents, flavouring agents, solubilizers, lubricants, suspending agents, binders and disintegrating agents.

Generally, the medicament is administered in doses between 0.1 and approximately 5 mg/kg/day of the peptide derivative of formula (I). It can be used as an analgesic or hypothermal agent or for the treatment of certain arterial hypertensions.

EXAMPLE 1

Preparation of the Peptide Derivative of Formula

This derivative, designated hereinafter by the term phosphodiepryl O3, is a derivative in accordance with formula (I), in which $R^1$ is the phenylethyl group, $R^2$ the proline derivative, $R^3$ a hydrogen atom, $R^4$ the n-butyl group and $R^5$ a hydrogen atom.

a) PREPARATION OF DIBENZYL PHENYL ETHYL PHOSPHONATE

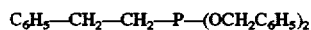

Careful mixing takes place in dimethyl formamide of 1 mmole of sodium hydride, under a nitrogen atmosphere and at −15° C. and to it is gradually added 1 mmole of dibenzyl phosphite dissolved in dimethyl formamide. The reaction is allowed to continue until all the hydrogen is given off.

This is followed by the addition, accompanied by stirring, of 1 mmole of phenyl ethyl bromide in dimethyl formamide, still under a nitrogen atmosphere, and said addition takes place sufficiently slowly for the temperature to vary from −10° to 0° C. When all the phenyl ethyl bromide solution has been added, the reaction mixture is then allowed to return to 25° C. The nitrogen is removed and stirring is maintained for 3 h.

This is followed by the evaporation of the dimethyl formamide (DNF) mixture under high vacuum, at a temperature of 35° to 40° C., followed by taking up in ether, washing twice the organic phase with water, followed by its drying on sodium sulphate. After evaporating the solvent, the desired dibenzyl phenyl ethyl phosphonate is obtained with an 80% yield.

This product is then purified by flash chromatography on silica using as the eluent a mixture of ether and ethyl acetate in a ⅔ volume ratio. This gives the purified phosphonate with a 40% yield.

b) PREPARATION OF THE MONOBENZYL PHENYL ETHYL PHOSPHONATE CHLORIDE 1 mmole of phosphorus pentachloride in benzene is added to a solution in benzene of 1 mmole of the previously obtained dibenzyl phenyl ethyl phosphonate. The mixture is heated to 70° C. under reflux and an anhydrous atmosphere for 3 to 4 h until the complete obtaining of the chloride. This is followed by the evaporation of the benzene of said mixture and it is taken up in dry dichloromethane. This solution is used immediately for carrying out the coupling with peptide.

c) COUPLING WITH PEPTIDE

To the solution of 1 mmole of monobenzyl phenyl ethyl phosphonate chloride in dichloromethane previously obtained is added at 0° C., 0.9 mmole of HCl peptide, Gly-Pro-Nle-OCH$_2$-C$_6$H$_5$, in dichloromethane and two equivalents of triethylamine. It is allowed to react accompanied by stirring for 30 minutes at 0° C. and then for an additional 30 minutes at 25° C. The dichloromethane is then evaporated and the oil taken up in ethyl acetate, followed by washing with water, with 0.1N hydrochloric acid, 5% NaHCO$_3$ and then with water to neutrality. The organic phase is dried and then evaporated. This gives the protected peptide derivative with a 90% yield. This derivative is purified by flash chromatography using as the elution solvent the dichloromethane—methanol mixture (9/1 by volume).

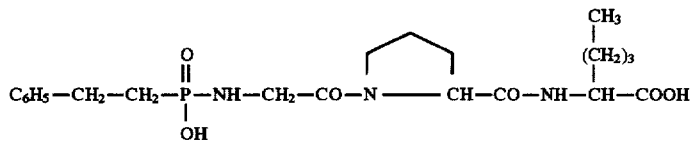

d) DEPROTECTION

The deprotection of the derivative takes place by catalytic hydrogenation using palladium as the catalyst and this gives phosphodiepryl O3.

EXAMPLES 2 TO 7

Preparation of Peptide Derivatives

These examples use the operating procedure of example 1 for preparing the peptide derivatives of the attached Table 1 and in stage a) the corresponding phosphonate is prepared by the same process as that described for $C_6H_5—(CH_2)_2—P—(OCH_2C_6H_5)_2$ and coupling with the appropriate peptide takes place instead in stage c).

EXAMPLE 8

Use of Phosphodiepryl O3 as the Inhibitor of Endopeptidase 24.16

Incubation takes place for 1 h at 37° C. of 5 nmole (50 μm/l) of Mcc-Pro-Leu-Gly-Pro-DLys-Dnp, which is a known endopeptidase 24.16 substrate, Mcc representing the 7-methoxycoumarin-3-carboxyl radical and Dnp the 2,4-dinitrophenyl radical, with 10 μl of purified endopeptidase 24.16 in a final volume of 100 μl of the Tris-HCl-50 mM, pH 7.5 buffer in the absence of inhibitor (control) or in the presence of phosphodiepryl O3 at concentrations between $10^{-11}$ and $10^{-7}$ mole/l. After incubating for 1 h, the solutions are analyzed by fluorimetry, as described by Dauch et al, Biochem. J., 280, pp.421–426, 1991a.

The results obtained are given in FIG. 1, which represents the fluorescence (in % of the fluorescence of the control as a function of the phosphodiepryl O3 concentration in mole/l, expressed in logarithmic coordinates). FIG. 1 shows that endopeptidase 24.16 is inhibited by phosphodiepryl O3 and that the inhibition rate increases with the inhibitor concentration. The inhibitor concentration inhibiting 50% endopeptidase, IC50, is 1 nM and the inhibition constant Ki is 0.3 nM.

Thus, the inhibiting properties of phosphodiepryl O3 are far superior to those of the known inhibitor Pro-Ile (Ki=90 μM).

EXAMPLE 9

Inhibition of Endopeptidase 24.16

This example, like example 8, studies the inhibiting effect of phosphodiepryl O3 on endopeptidase 24.16, but in this case neurotensin is used as the enzyme substrate.

To this end, 2 nmole (20 μM) of neurotensin are incubated at 37° C. with 10 μl of endopeptidase 24.16 in a final volume of 100 μl of Tris-HCl, 50 mM, pH 7.5 buffer in the absence of inhibitor (control) or in the presence of phosphodiepryl O3 concentrations between $10^{-10}$ and $10^{-6}$ mole/l. After incubation, it is interrupted by acidification and the solution analyzed by high performance liquid chromatography (HPLC) using an elution system constituted by a linear gradient of 42 min of 0.1% trifluoroacetic acid and 0.05% triethyl amine in acetonitrile, ranging between 9/1 and 3/1, as described by Checler et al, Biochimie 70, pp.75–82, 1988.

The results obtained are given in FIGS. 2 to 7, which show chromatograms obtained by measuring the optical density at 230 nm as a function of time (min).

Figure 2:
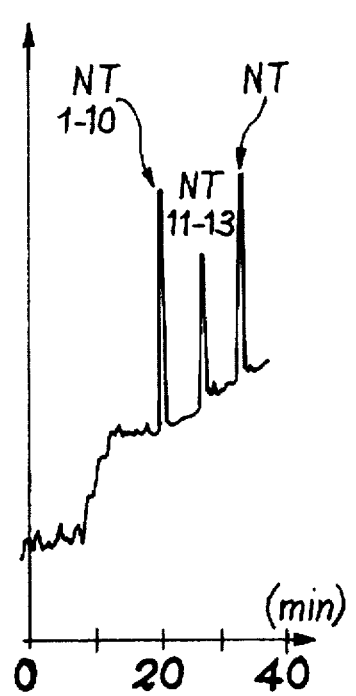
FIGS. 2 to 7 Chromatograms obtained during inhibition tests on endopeptidase 24.16.
Figure 3:
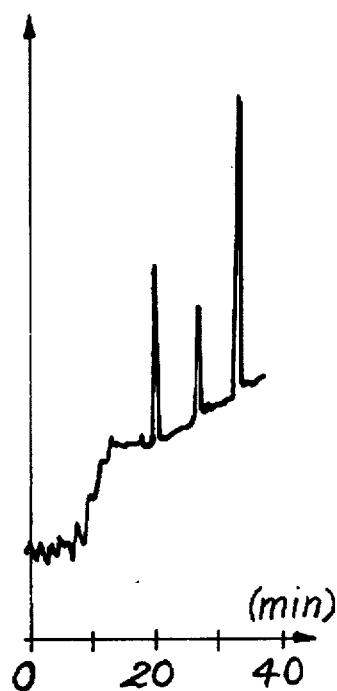
Figure 4:
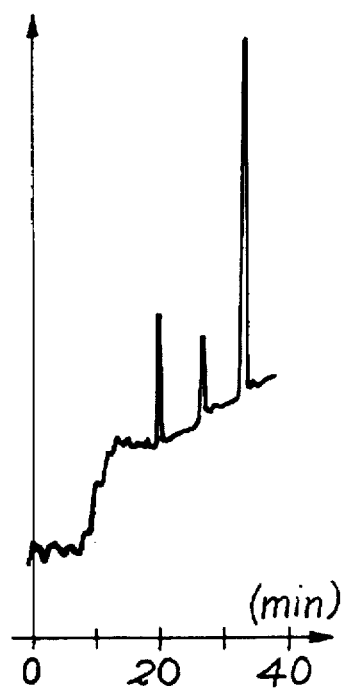
Figure 5:
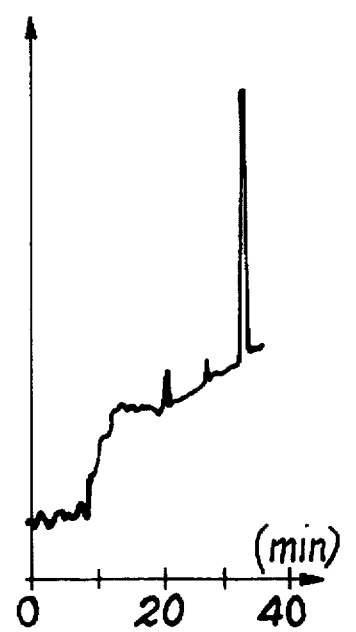
Figure 6:
Figure 7:
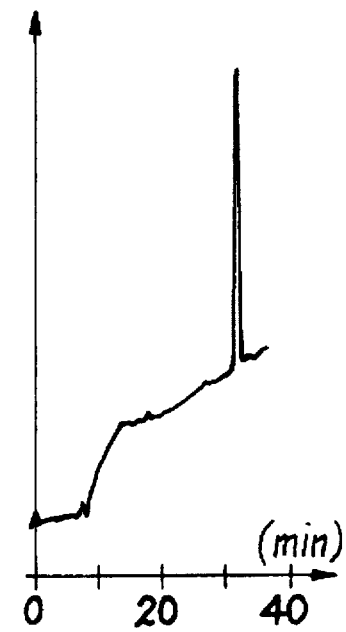

FIG. 2 shows the chromatogram obtained in the absence of an inhibitor. It is possible to see 3 peaks respectively corresponding to neurotensin 1-10 (NT 1-10), neurotensin 11-13 (NT 11-13) and neurotensin (NT). Neurotensin 1-10 and neurotensin 11-13 are degradation products of the starting neurotensin.

FIGS. 3 to 7 show that the peaks corresponding to degraded neurotensin (neurotensin 1-10 and 11-13) decrease with the inhibitor concentration.

Figure 8:
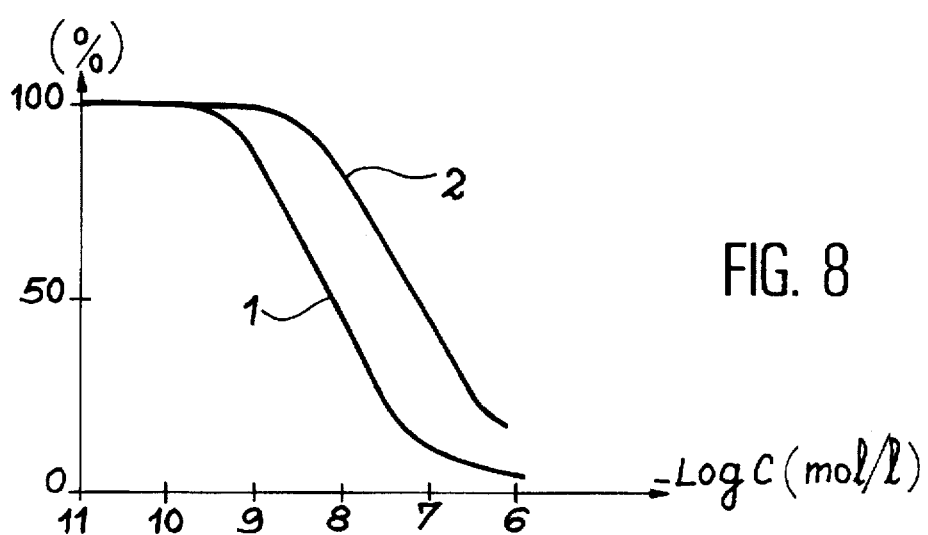
FIG. 8 Curves representing the percentage inhibiting effect of a derivative according to the invention on endopeptidase 24.16 (curve 1) and on endopeptidase 24.15 (curve 2) as a function of the inhibitor concentration.

FIG. 8 (curve 1) shows the inhibition rate (in %, based on the control) as a function of the concentration C (in mole/l) of inhibitor (in logarithmic coordinates). On the basis of this curve, the inhibition values IC50=10 nM and Ki=0.9 nM are obtained. If this value is compared with the Ki obtained with the known inhibitor Pro-Ile (90 μM), it can be seen that the inhibitor according to the invention is 100,000 times more effective.

EXAMPLE 10

Inhibition of Endopeptidase 24.15

This example studies the inhibition of endopeptidase 24.15 by phosphodiepryl O3 using as the substrate for said enzyme Bz-Gly-Ala-Ala-Phe-pAg, with Bz representing the benzoyl radical and pAB paraaminobenzoate.

To this end, 5 nM of said substrate are incubated at 37° C. with 10 μl of post-hydroxylapatite fractions of endopeptidase 24.15 in the absence (control) or in the presence of increasing phosphodiepryl O3 concentrations. Following incubation, acidification and HPLC analysis on an inverse phase take place using a linear gradient elution system of 63 min of 0.1% trifluoroacetic acid and 0.05% triethyl amine in acetonitrile between 9/1 (v/v) and 5.5/4.5 (v/v), as described by Checler et al in Biochimie 70, pp.75–82, 1988.

Figure 9:
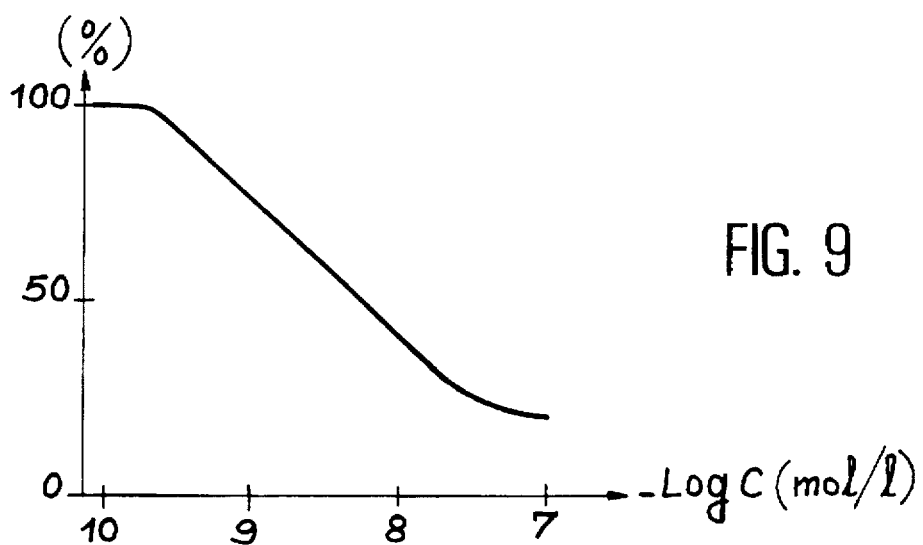
FIG. 9 A curve of the percentage inhibiting effect of the derivative according to the invention on endopeptidase 24.15 as a function of the inhibitor concentration.

The results obtained are given in FIG. 9, which shows the inhibition rate (in % based on the control), as a function of the concentration C (in mole/l) of inhibitor in logarithmic coordinates. It can be seen that the inhibition regularly increases with the inhibitor concentration. The inhibition values are IC50=5 nM and Ki=5 nM.

EXAMPLE 11

Inhibition of Endopeptidase 24.15

This example uses the same operating procedure as in example 10, but using neurotensin as the endopeptidase 24.15 substrate.

To this end, incubation takes place of 2 nmole of neurotensin at 37° C. with 10 μl of post hydroxylapatite endopeptidase 24.15 fractions in the absence (control) or in the presence of increasing phosphodiepryl O3 concentrations. After incubating for 42 min, acidification and analysis takes place of the liquid phase by HPLC in reverse phase using linear gradients of the trifluoroacetic acid, triethyl amine and acetonitrile system, as in example 3.

Curve 2 of FIG. 8 illustrates the results obtained. On the basis of this curve, it is possible to determine IC50 and the inhibition constant Ki, giving IC50=100 nM and Ki=7.5 nM.

Thus, phosphodiepryl O3 is also a very effective inhibitor of endopeptidase 24.15.

The attached Table 2 gives the values of Ki and IC50 obtained in examples 8 to 11.

EXAMPLE 12

Effects of Phosphodiepryl on Carboxypeptidase A

In this example, incubation takes place for 15 min at 37° C. of a carboxypeptidase A substrate constituted by 5 nmole of Hippuryl-Phe with 0.2 μg of carboxypeptidase A treated by DP in a final volume of 100 μl of Tris-HCl, 50 mM, pH 7.5 buffer, in the absence or presence of 1 μmole/l of phosphodiepryl O3. After 15 min incubation, the solution is analyzed by HPLC. The results obtained show that the presence of 1 μmole/l of phosphodiepryl O3 gives rise to no carboxypeptidase A inhibition.

EXAMPLE 13

Effects of Phosphodiepryl 03 on Leucine Aminopeptidase

In this example 5 nM of a leucine aminopeptidase substrate constituted by Leu-7AMC are incubated for 15 min end at 37° C. with 0.02 μg of leucine aminopeptidase in a final volume of 100 μl of Tris-HCl, 50 mM, pH 7.5 buffer, in the absence or presence of 1 μmole/l of phosphodiepryl 03. After incubating for 15 min, the reaction medium is analyzed by HPLC. The results obtained show that there is no inhibition by phosphodiepryl 03.

EXAMPLE 14

Effects of Phosphodiepryl 03 on the Angiotensin Conversion Enzyme

Incubation takes place for 15 min at 37° C. of 5 nmole of Hippuryl-His-Leu with 0.6 μg of angiotensin conversion enzyme in a final volume of 100 μl of Tris-HCl, 50 mM, pH 7.5 buffer containing 0.3 mole/l of NaCl in the absence or presence of 1 μmole/l of phosphodiepryl 03. The solution is analyzed by HPLC and it is found that there is no inhibition of the angiotensin conversion enzyme by phosphodiepryl 03.

EXAMPLE 15

Effect of Phosphodiepryl 03 on Endopeptidase 24.11

The hydrolysis of 2 nM of neurotensin is followed by 9 μg of endopeptidase 24.11 under the conditions described in example 3. The results obtained show that there is no inhibition of endopeptidase 24.11 by phosphodiepryl 03.

Thus, the phosphodiepryl 03 according to the invention is of great interest, because it has a powerful inhibiting action against endoproteases 24.16 and 24.15, whereas it has no effect on other proteases such as carboxypeptidase A, leucine aminopeptidase, angiotensin conversion enzyme and endopeptidase 24.11. Therefore this peptide derivative is specific and selective for endopeptidases 24.15 and 24.16.

EXAMPLE 16

Inhibition of Endopeptidase 24.16

As in example 9, this example studies the inhibiting effect of the compounds of examples 1 to 7 on endopeptidase 24.16 using neurotensin as the substrate and operating in the same way, except that use is made of a Tris-HCl, 25 mM, pH 7 buffer and a temperature of 25° C.

The results obtained are given in Table 3, which also indicates the results obtained with a peptide derivative having a methyl group in $R^1$ instead of an aralkyl group.

EXAMPLE 17

Inhibition of Endopeptidase 24.15

As in example 11, this example studies the inhibiting effect of the compounds of examples 1 to 7 on endopeptidase 24.15 using neurotensin as the substrate and working under the same conditions, except that use is made of a Tris-HCl 25 mM, pH 7 buffer and a temperature of 25° C.

The results obtained are given in Table 3 which also indicates the results obtained with the peptide derivative having a methyl group in $R^1$. The results of Table 3 clearly show the effectiveness of the peptide derivatives according to the invention, particularly the effect of groups $R^1$ and $R^2$. Thus, when using for $R^1$ a methyl group, the results are inferior and this is also the case when Pro is replaced by Ala.

TABLE 3

| Compound | Endopeptidases 24.16 Ki (nm) | 24.15 Ki (nm) |
|---|---|---|
| $C_6H_5-(CH_2)_2-P(=O)(OH)-Gly-Pro-Nle$ | 0.44 | 1.6 |
| $C_6H_5-CH_2-P(=O)(OH)-Gly-Pro-Nle$ | 21 | 30 |
| $C_6H_5-(CH_2)_3-P(=O)(OH)-Gly-Pro-Nle$ | 14 | 15 |
| $C_6H_5-(CH_2)_2-P(=O)(OH)-Ala-Pro-Nle$ | 0.36 | 0.48 |
| $C_6H_5-(CH_2)-P(=O)(OH)-Gly-Ala-Nle$ | 27 | 50 |
| $C_6H_5-(CH_2)_2-P(=O)(OH)-Gly-Pro-Ala$ | 3 | 6 |
| $C_6H_5(CH_2)_2-P(=O)(OH)-Gly-Pro-Tyr$ | 5 | 7 |
| $CH_3-P(=O)(OH)-Gly-Pro-Nle$ | 105 | 223 |

TABLE 2

| Ex. | Enzyme | Substrate | IC$_{50}$ (nM) | K$_i$ (nM) |
|---|---|---|---|---|
| 8 | endopeptidase 24.16 | Mcc—Pro—Leu—Gly—Pro—DLys—Dnp | 1 | 0.3 |
| 9 | endopeptidase 24.16 | neurotensin | 10 | 0.9 |
| 10 | endopeptidase 24.15 | Bz—Gly—Ala—Ala—Phe—pAB | 5 | 5 |
| 11 | endopeptidase 24.15 | neurotensin | 100 | 7.5 |

TABLE 1

| Ex | Compound | R¹ | R² | R³ | R⁴ | R⁵ | R⁶ | R⁷ |
|---|---|---|---|---|---|---|---|---|
| 2 | $C_6H_5-CH_2-\overset{O}{\underset{OH}{\overset{\|\|}{P}}}-Gly-Pro-Nle$ | $C_6H_5-CH_2$ | $-N\overset{\frown}{\phantom{xxx}}CH-CO-$ | H | $-(CH_2)_3-CH_3$ | H | H | H |
| 3 | $C_6H_5-(CH_2)_3-\overset{O}{\underset{OH}{\overset{\|\|}{P}}}-Gly-Pro-Nle$ | $C_6H_5-(CH_2)_3-$ | " | " | " | " | " | " |
| 4 | $C_6H_5-(CH_2)_2-\overset{O}{\underset{OH}{\overset{\|\|}{P}}}-Ala-Pro-Nle$ | $C_6H_5-(CH_2)_2-$ | " | " | " | " | " | $CH_3$ |
| 5 | $C_6H_5-(CH_2)_2-\overset{O}{\underset{OH}{\overset{\|\|}{P}}}-Gly-Ala-Nle$ | " | $-NH-\overset{CH_3}{\underset{\|}{C}H}-CO-$ | " | " | " | " | H |
| 7 | $C_6H_5-(CH_2)_2-\overset{O}{\underset{OH}{\overset{\|\|}{P}}}-Gly-Pro-Ala$ | " | $-N\overset{\frown}{\phantom{xxx}}CH-CO-$ | " | $CH_3$ | " | " | " |
| 7 | $C_6H_5(CH_2)_2-\overset{O}{\underset{OH}{\overset{\|\|}{P}}}-Gly-Pro-Tyr$ | " | " | " | $-CH_2-C_6H_4-OH$ | " | " | " |

We claim:

1. A method of inhibiting endopeptidase 24.15 or endopeptidase 24.16 in a patient, comprising administering a composition comprising an effective amount of a peptide derivative of formula (I):

$$R^1-\overset{O}{\underset{OR^6}{\overset{\|\|}{P}}}-NH-\underset{R^7}{\overset{\|}{C}H}-CO-R^2-\underset{R^3}{\overset{R^4}{\overset{\|}{N}}}-CH-COOR^5 \quad (I)$$

wherein $R_1$ is an aralkyl group, whose alkyl group has 1 to 3 carbon atoms, the aralkyl group being unsubstituted, and the aryl part being phenyl or naphthyl;

R2 is a divalent radical of formula:

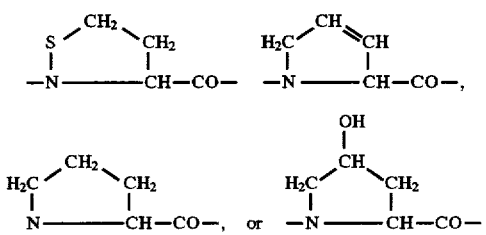

connected by its NH part to CO;

R3 is a hydrogen atom or a C1 to C4 alkyl group;

R4 is selected from the group consisting of C1 to C5 alkyl and side chains of α-amino acids;

R5 is a hydrogen atom, $NH_4+$, a pharmaceutically acceptable metal ion, a C1 to C5 alkyl group or a benzyl group;

R6 is a hydrogen atom, $NH_4+$ or a pharmaceutically acceptable metal ion; and

R7 is H or $CH_3$;

to a patient in need thereof.

2. The method of claim 1, wherein R2 is the radical

3. The method of claim 1, wherein R1 is phenylethyl.

4. The method of claim 1, wherein R3 is a hydrogen atom, and R4 is selected from the group consisting of n-butyl, methyl, and p-hydroxyphenylmethyl.

5. The method of claim 1, wherein R5 and R6 are hydrogen.

6. The method of claim 1, wherein said peptide derivative has the formula:

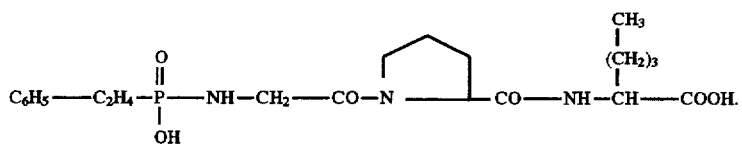

7. The method of claim 1, wherein said peptide derivative has the formula:

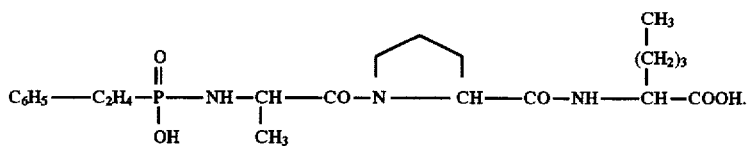

8. The method of claim 1, wherein $R^1$ is benzyl.
9. The method as claimed in claim 1, wherein $R^1$ is phenylpropyl.
10. A method of treating hypertension in a mammal comprising the steps of:
(a) assaying the following compounds for their ability to inhibit endopeptidase 24.15 or 24.16:

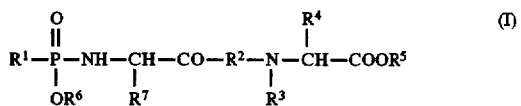

wherein $R^1$ is an aralkyl group, whose alkyl group has 1 to 3 carbon atoms, the aralkyl group being unsubstituted and the aryl part being phenyl;

$R^2$ is a divalent radical of formula:

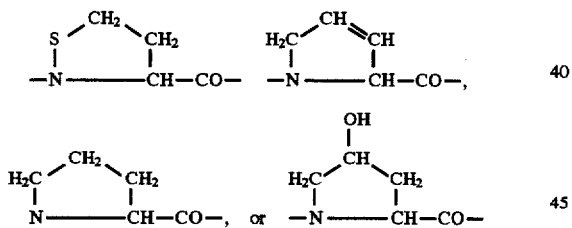

connected by its NH part to CO;

$R^3$ is a hydrogen atom or a $C_1$ to $C_4$ alkyl group;

$R^4$ is selected from the group consisting of $C_1$ to $C_5$ alkyl and side chains of α-amino acids;

$R^5$ is a hydrogen atom, $NH_4^+$, a pharmaceutically acceptable metal ion, a $C_1$ to $C_5$ alkyl group or a benzyl group;

$R^6$ is a hydrogen atom, $NH_4^+$ or a pharmaceutically acceptable metal ion, and $R^7$ is H or $CH_3$; and (b) administering the compound to said mammal when the compound exhibits in vitro inhibition of said endopeptidase 24.15 or 24.16.

11. The method of claim 10, wherein the compound exhibits a $K_i$ of about 0.3–50 nM or an $IC_{50}$ of 2–100 nM.

12. The method of claim 11, wherein the compound exhibits a $K_i$ of about 0.3–50 nM.

13. The method of claim 11, wherein the compound exhibits an $IC_{50}$ of 2–100 nM.

* * * * *